United States Patent [19]

Törnblom

[11] Patent Number: 4,853,634
[45] Date of Patent: Aug. 1, 1989

[54] DEVICE FOR CRACK DETECTION ON HOT CAST BILLETS AND SUPPRESSING THE EFFECTS OF MAGNETIC REGIONS

[75] Inventor: Bengt H. Törnblom, Västerås, Sweden

[73] Assignee: Törnbloms Kvalitetskontroll AB, Västerås, Sweden

[21] Appl. No.: 85,173

[22] Filed: Aug. 14, 1987

[30] Foreign Application Priority Data

Aug. 27, 1986 [SE] Sweden ................ 8603604

[51] Int. Cl.⁴ ............ G01N 27/72; G01R 33/12
[52] U.S. Cl. .................. 324/225; 324/226; 324/227; 324/232
[58] Field of Search ............ 324/225, 226, 227, 233, 324/232

[56] References Cited

U.S. PATENT DOCUMENTS 3,848,182 11/1974 Gerner et al. ............ 324/233

Primary Examiner—Reinhard J. Eisenzopf
Assistant Examiner—Walter E. Snow
Attorney, Agent, or Firm—Watson, Cole, Grindle & Watson

[57] ABSTRACT

An electrical defect testing device for a non-magnetic test object, for example crack detection on hot continuously cast billets, is provided with means for detecting and suppressing the influence of disturbing magnetic regions of the object (e.g. regions of cold oxide scale). The device comprises at least one sensing transducer for harmful faults which is adapted to move relative to the test object. At least one detector is associated with the transducer for identifying the presence of magnetic material, and a blocking circuit is provided which, directly or indirectly, is controlled by the magnetic detector and is used for suppressing signals originating from a fault vector, for example a signal indicating a harmful fault. The presence of magnetic material can be detected using an eddy current technique.

25 Claims, 3 Drawing Sheets

DEVICE FOR CRACK DETECTION ON HOT CAST BILLETS AND SUPPRESSING THE EFFECTS OF MAGNETIC REGIONS

TECHNICAL FIELD

The present invention relates to a device for the non-destructive testing of a basically non-magnetic test object, for example crack detection of a hot continuously cast steel billet and for detecting and suppressing the influence of disturbing magnetic regions and/or material, for example cold oxide scales. The invention relates, among other things, to the field of control and/or supervision.

The invention can, for example, be regarded as an important reliability-improving complement, which warns of the presence of disturbing magnetic material, to known crack detection equipment.

DISCUSSION OF PRIOR ART

The fact that the permeability gives rise to disturbing vectors of varying magnitudes, when $\mu_r > 1$, has long been a well-known problem in eddy current testing of non-magnetic material. Heretofore, various attempts have been made to remove the magnetic material for example, magnetic oxide scales and the like by, for example, flushing the hot billet surface with water under high pressure, which is both expensive and time-consuming and not particularly efficient.

As far as is known, the existing specialist literature does not describe any method or device corresponding to what is described herein. The basic idea behind the invention is to first detect the presence of magnetic material and then to alert and control the crack detection. Although much of what is shown in the impedance diagram in FIG. 1 is known to the expert, as far as is known to me nobody has attempted to draw or succeeded in drawing, the conclusions which form the basis of the present invention. A probable explanation of this may be that the permeability, as opposed to the electrical conductivity, is not of major interest to, for example, an end user of steel ingots, such as slabs and the like, but has only been a problem facing users of eddy current testing equipment.

A primary object of the invention is to detect the occurrence of magnetic material and to warn of its presence and effects, in order thus to be able to ensure that the magnetic disturbances are not confused with harmful faults (e.g. actual cracks).

SUMMARY OF THE INVENTION

A non-destructive testing device according to the invention comprises at least one transducer or fault sensor, which is adapted to move relative to a test object, and at least one detector, associated with the fault sensor, the task of which is to detect the possible occurrence of disturbing magnetic regions and/or material, and at least one blocking means directly or indirectly controlled by the magnetic detector, for suppressing signals originating from the fault sensor, for example a crack signal. The invention is characterized in that the magnetic regions and/or magnetic material is adapted to be detected using an eddy current technique, and that signals originating from magnetic material are adapted to be separated from signals originating from a fault.

It would, of course, be possible to measure the surface temperature of the test object by means of, for example, radiation pyrometers and the like, and thereby to determine whether the material is expected to be magnetic or not. However, for reasons which are easily understood, this method suffers from several serious drawbacks.

The invention enables, for example, the combination of detection of cracks and detection of magnetic material by means of, for example, a single eddy current transducer. Also, certain parts of the electronic measuring equipment may be used in common. This entails advantages both from the point of view of economy and from the point of view of ease of measuring technique.

In eddy current testing, for example crack detection, of non-magnetic material, it is assumed that there is no magnetic permeability in the material, i.e. that the test object is fully non-magnetic. By non-magnetic material is meant, for example, steel ingots such as slabs and billets, the temperature of which, at the time of measuring, lies above the so-called Curie temperature or Curie point. It may also be a non-magnetic steel tube which, via conventional saturation magnetization, has received an apparent permeability largely corresponding to $\mu_o$. In all these cases it may occur that foreign magnetic particles and the like are present in or on the material, or that, for example, a certain limited spot on the hot billet surface, because of a partially low surface temperature, has become locally magnetic.

In continuous casting processes, the temperature of the cast strand may vary owing to different process parameters, which are changed during a continuing casting process. In this case, the billet surface is often coated with oxide scales of varying sizes, the Curie temperature of which is often somewhat lower than that of the steel itself. Nevertheless it may happen that the oxide scales, which contain $FeO$, $Fe_2O_3$ and $Fe_3O_4$, because of poor thermal contact with the billet sometimes have a temperature which is below their Curie temperature, whereby they become magnetic and then become a disturbing influence on the eddy current testing equipment provided to monitor for harmful faults in the billet.

It is important to note in this connection that no matter what is the reason for the presence of magnetic material in or on the test object, its presence is without exception disturbing in view of eddy current testing adapted to non-magnetic test objects, and particularly in the case of the so-called multifrequency testing.

The present invention aims to provide a solution to the problems mentioned above and other problems associated therewith.

The invention can be regarded as an important complement to the following Swedish patents/patent applications: 7507857-6, 7613708-3 (corresponding to U.S. Pat. No. 4,237,419), 7813344-4 (corresponding to G.B. Pat. No. 2,041,535), 8206678-8 (corresponding to PCT/SE83/00409 continued as U.S. application Ser. No. 826,850), 8302738-3 (corresponding to PCT/SE83/00175 continued as U.S. Pat. No. 4,646,013), 8400698-0 (corresponding to U.S. application Ser. No. 699,594 filed on Feb. 8th 1985 in the name of Bengt H. Tornblom, now U.S. Pat. No. 4,661,777), 8400861-4 (corresponding to U.S. application Ser. No. 702,314 filed on Feb. 15th 1985 in the name of Bengt H. Törnblom , now U.S. Pat. No. 4,703,265), 8601785-2, 8603113-5 and 8603240-6. The terminology and the drawings used in these patents/applications are also applicable, in parts, to the present invention and where permitted the disclosures of these prior applications are herein incorporated by reference.

In a preferred embodiment, at least one quantity, for example a cold oxide scale, or a combination of quantities, for example a crack in an oscillation mark, as a function of a comparison of signals originating from at least two transformation blocks and/or normalization settings are adapted to be separated.

Since the majority of the above-mentioned patent documents relate to crack detection on hot, non-magnetic material, magnetic disturbance may be expected to arise, which justifies the present invention being used as a complement thereto.

The following terms will be used in the specification and should be taken to have the meaning given.

By EDDY CURRENT TESTING is meant control and/or measurement based on the use of frequencies and/or frequency components within a range extending from a few Hz to several MHz.

By FREQUENCY is means that frequency with which a transducer or sensor is supplied and includes a carrier frequency. The term "frequency" also includes a frequency component.

By TEST OBJECT is meant, for example, a continuously cast billet, a rod, a tube, a sheet, or a volume of liquid molten steel. The term "test object" also embraces particles and objects on the surface of the test object, for example oxide scales and the like.

By FAULT SENSOR is meant, for example, a surface transducer coil supplied with current, which coil moves, for example, in planes parallel to the surface of the test object or part of the surface.

By LIFT-OFF (LO) is meant the distance of the fault sensor relative to the surface of the test object. (See also the above-mentioned patents/applications.)

By MAGNETIC material is meant that the material is influenced by a permanent magnet, i.e. that the relative permeability is $\mu_r > 1$.

By FAULT VECTOR (FV) is meant that vector which is caused by a harmful fault, for example, by a crack in the impedance plane of the fault sensor (for example, as shown in FIG. 1).

By $\mu$ VECTOR ($\mu V$) is meant that vector which is caused by the magnetic material (for example, as shown in FIG. 1).

By VECTOR LOBE (VL) is meant that area in the impedance plane within which fault vectors (of varying depths and vertical positions) are situated.

The following description assumes that the reader has a certain basic knowledge of impedance diagrams, etc., and therefore the more elementary bases and details have been omitted in order to keep the description to acceptable lengths. To restrict the scope of the description, an application of the invention will be described in which the device is based on eddy current technique. However it should be appreciated that other techniques, for example leakage fluxes, as well as the use of sensors of the Hall element type, and so on, are embraced by the invention and the following description should be read with that in mind.

BRIEF DESCRIPTION OF THE DRAWINGS

The invention will now be described in greater detail, by way of example, with reference to the accompanying drawings, wherein.

DESCRIPTION OF PREFERRED EMBODIMENTS

Figure 1:
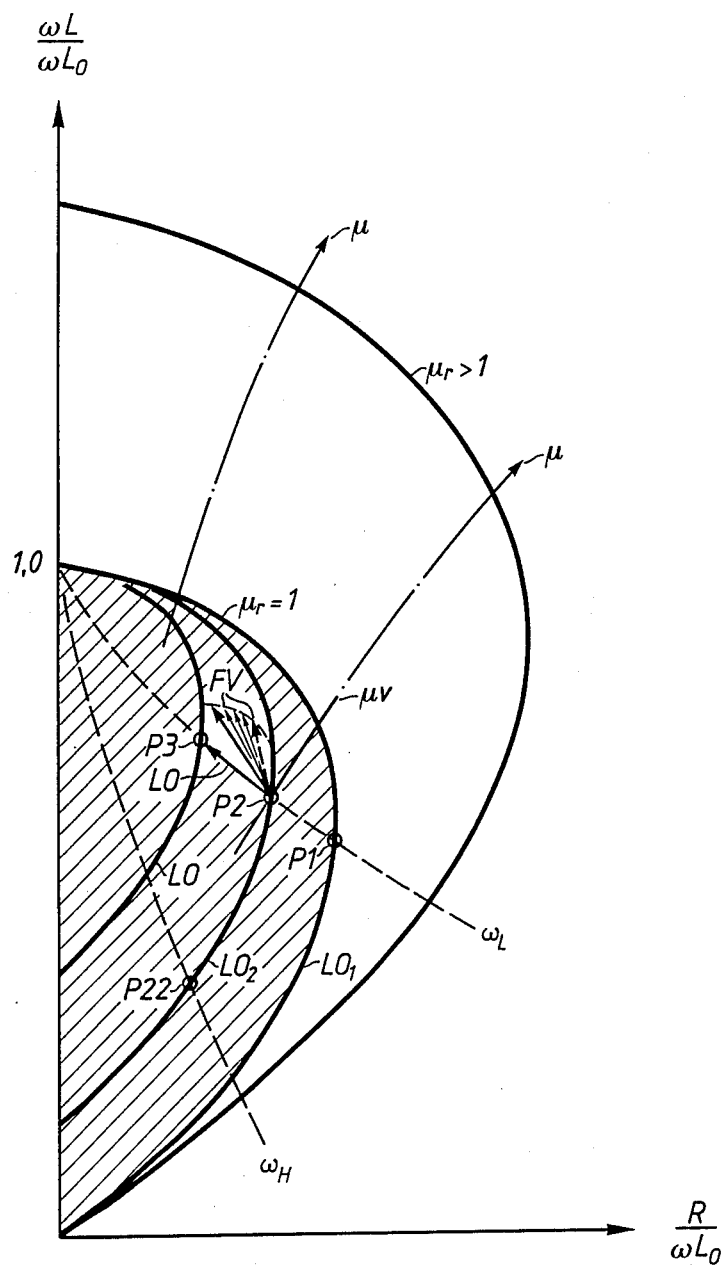
FIG. 1 shows a normalized impedance diagram for a conventional crack detection transducer or sensor.

FIG. 1 shows a normalized impedance diagram, of conventional character, for a transducer/sensor. The above-mentioned U.S. Pat. No. 4,646,013 shows in FIG. 3 a corresponding impedance diagram in the case of a test object of non-magnetic material i.e. the impedance curves are based on $\omega L/\omega L_O = 1.0$. In the accompanying FIG. 1, however, the impedance plane has been supplemented with curves for a magnetic material, in other words, $\mu_r > 1$. As will be clear, the permeability, $\mu$, has an amplification effect on the electric impedance, which may greatly disturb the eddy current measurement of cracks and the like defects, especially when the cracks have a direction in the impedance plane which largely coincides with the $\mu$-direction. The magnetic permeability has a direction in the impedance plane as is clear from the $\mu$-vectors and the dot-dashed lines displayed on the graph.

In, for example, crack detection on hot (>780° C.) steel ingots, the temperatures of which exceeds the Curie temperature the steel is non-magnetic. If a simple surface transducer is used for crack detection and the distance of the transducer to the billet surface varies, for example between $LO_2$ and $LO_3$, the impedance of the transducer also varies. This impedance variation has different magnitudes at different carries frequencies, and for a certain frequency, $\omega_L$ in FIG. 1, it is shown as a vector LO between points P2 and P3. Depending on the direction of the LO-movement, this vector may reverse its direction, that is it may change polarity.

The $LO_1$-curve in FIG. 1 represents a strong inductive coupling between the transducer and the test object, for example coupling such as would occur when LO=0 (i.e. the transducer is in contact with the surface). It is also possible, for example to define the $LO_1$-curve as the smallest LO-distance which is possible in practice. For the non-magnetic material, this then means that the impedance curves are contained within the sectioned part of FIG. 1.

Figure 2:
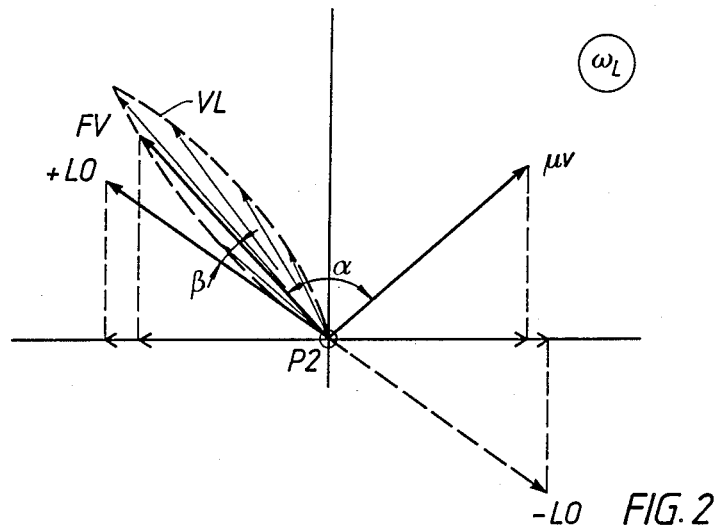
FIGS. 2 and 3 show separate vector lobes extracted from the diagram of FIG. 1, and FIGS. 4 and 5 show schematically two practical arrangements of device according to the invention.

Now, let it be assumed that the transducer is at the distance $LO_2$ from the surface of the test object and that we are studying the carrier frequency $\omega_L$, which means that we are at point P2 in FIG. 2. When the transducer is positioned over a crack, a so-called fault vector (FV) is obtained, the direction of which lies near the LO-direction, which is described in detail in the above-mentioned U.S. Pat. No. 4,646,013. Now, if the test object for some reason should become magnetic, i.e. $\mu_r > 1$, a vector would be obtained in a corresponding manner, which in FIG. 1 is shown as a vector $\mu V$. It should be pointed out here that the vectors FV and $\mu V$ after detection have different signal frequency contents, i.e. different duration, which is due to the fact that the crack has an appearance which is different from (shorter than, for example), the magnetic region on the test object, which may be an increased thickness of oxide scale. These vectors, which are often of a differential nature, have, for two different carrier frequencies, $\omega_L$ and $\omega_H$, been separated from FIG. 1 and are plotted graphically in FIGS. 2 and 3. These vectors can be conventionally transformed into, for example, voltages which may be rectified via, for example, phase-controlled rectifiers. In this way, it is possible to separate vectors having different directions, i.e. different phase positions, in the impedance diagram.

Figure 3:
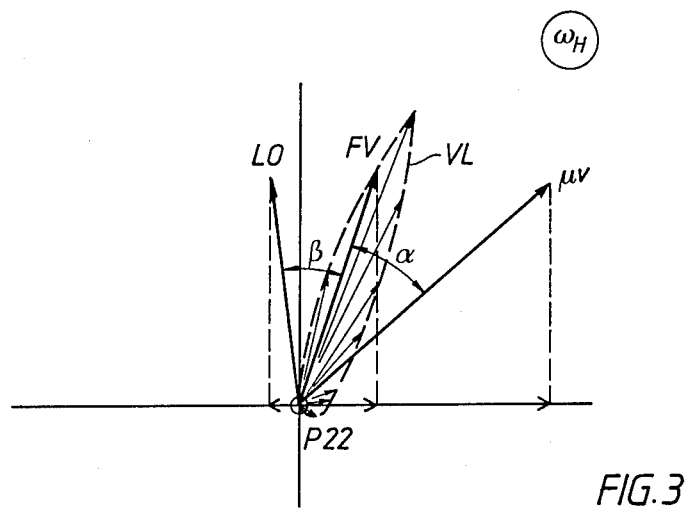

When using the term vector, this is often understood to include also a signal, for example an alternating voltage, the phase position of which represents the direction of the vector and the amplitude of which corresponds to the magnitude of the vector. In FIGS. 2 and 3 the so-called vector lobes (VL) have been indicated in dashed lines. These lobes indicate the limiting surface within which fault vectors of a varying depth and vertical position are located. In the case of unusually large cracks, the length of the lobe may be greater.

Especially in the case of lower frequencies, $\omega_L$ (for example $< 100$ KHz) the angle $\alpha$ between FV and $\mu$V is close to 90°, whereas, on the other hand, at higher frequencies, $\omega_H$ (for example 1 MHz) the angle $\alpha$ is distinctly smaller than 90°. From the point of view of phase discrimination, of course, it is advantageous if the angle $\alpha$ is large (for example 90°) if it is desired, as in the present case, to separate $\mu$V from FV.

From FIG. 3 it is clear that the lower righthand part of the vector lobe VL intersects the $\mu$-vector, $\mu$V. This part of the vector lobe usually represents cracks located somewhat deeper in the material, i.e. cracks not open to the surface. The consequence of this is that at higher frequencies there are cracks whose direction in the impedance diagram coincides with the $\mu$-direction. In other words, FV and $\mu$V cannot be separated in a reliable manner using phase discrimination at higher frequencies. On the other hand, at a suitably selected low frequency, as shown in FIG. 2, separating VL from $\mu$V, and inversely, does not present any problem, as in this case no intersection occurs. As far as is known, this fact has not been made use of by anyone in order to increase the relaibility in crack detection, as described in the present application.

As a first step towards a reliable separation of the $\mu$-vector from the other vectors, a suitable, often low, frequency is chosen which enables separation of $\mu$V from FV. As a second step, for example, the lift-off (LO) vector is suppressed. It is to be noted here that LO may change polarity, which in FIG. 2 is marked by $+$LO and $-$LO, respectively. Therefore, if, as indicated in FIG. 2, detection is carried out in a direction which is horizontal, the respective vector projection on the horizontal line will be approximately the same for $\mu$V and $-$LO, which means that it is impossible in this way to separate $\mu$V from $-$LO. On the other hand, as can be seen, at $\omega_L$ and horizontal projection of FV and $\mu$V, these can be separated from each other in an excellent way since the projections of FV and $\mu$V have different signs, which are easily distinguished between by electronic means. At a sufficiently low frequency where the angle $\alpha$ or the sum of the angles $\alpha$ and $\beta$ is of the order or magnitude of 90°, it is possible relative-ly efficiently to suppress the LO-influence by detecting the vectors largely perpendicular to the LO-direction or the FV-direction, depending on which of these is the most disturbing for the $\mu$-vector separation.

In the case of normal surface cracks, the angle $\beta$ is often $<18°$, which means that the fault vector is also suppressed relatively well when detecting $\mu$ perpendicular to the LO-direction. Because of the somewhat incomplete suppression of FV, however, it may be useful to improve the suppression via a filtering method. To this end, the fact that the frequency contents in the detected and rectified fault vector FV is higher than the frequency contents in the corresponding $\mu$-vector signal and the LO-vector signal, is employed. The filters for the respective vector types are therefore tuned to different signal frequencies, whereby they can be more easily separated from each other. The reason for the different frequency contents is that cracks and the possible magnetic portions of the test object have different shape and propagation. The transducer is then located over the crack and over the magnetic portions for different periods of time.

Since the LO-signal also differs with respect to frequency from other signals or vectors, the LO-signal can also be separated or suppressed further via a filter method, if required. Another method of suppressing or separating the LO-signal is via so-called vector transformation. In this case at least one LO-signal, or part thereof, of a different carrier frequency origin is employed in order to compensate, for example to balance away, the LO-vector or a part thereof. The same technique can also be employed for separation and suppression of FV-signals and so on. The invention includes both separate and combined solutions of the principles mentioned here.

It should be observed that no matter when the solution looks like, at least one frequency must be chosen which is low enough for the angle $\alpha$ to be sufficiently large. Since the frequencies which are used for crack detection are normally relatively high, it is often desirable to use at least one separate frequency for the magnetic detection, for example a frequency within the range 1 to 10 KHz.

Regarding the choice of a suitable frequency for efficient $\mu$V- detection, it should also be known that the absolute value of the permeability decreases with increasing frequency because of the inherent inertia of the material with respect to rapid magnetic changes. It is thus advantageous from two points of view to choose a frequency working point on the upper part of the impedance plane: for one thing, $\mu$V will be larger, and for another, $\alpha$ will be greater. The upper third part of the impedance curve is then a good choice.

To prevent $\mu$-vectors from being confused with fault vectors, it is advantageous to use the detected presence of magnetic material for automatically blocking the crack detector so that no false cracks are indicated. At the same time, some form of alarm should be given, for example automatically, in order to draw attention to the fact that the crack detector has been temporarily blocked or is unreliable because of magnetic disturbances.

The presence of magnetic material can also be used as an indication that something is wrong in the process, for example that excessive cooling is occuring in the continuous casting machine. When alarm is given indicating the presence of magnetic material, it is also possible —for example, automatically and temporarily—to activate devices for the removal of oxide scale and the like magnetic material.

In certain cases, it may be desirable that alarm is given when the permeability level exceeds a certain set threshold value. For that reason, the permeability signal should be sensibly constant within the LO operating range of the transducer. This can be achieved by signal processing, for example amplifying, the $\mu$-signal as a function of the LO-signal.

In those cases where the same transducer is used both for the detection of cracks and for the presence of magnetic material, the following advantages, inter alia, may be obtained: The measurement takes place at the same time on the same surface part, so the measured values are the current ones and are related to each other. The permeability dependence of the crack detection is nearly exactly indicated because the same transducer is used for both measurements. The transducer arrangement is, of course, simpler and less expensive.

In crack detection, some form of transducer manipulator is often used to move the transducer or sensor over, for example a hot steel strand. The transducer may also consist of a so-called "whirligig" device i.e. it has a rotary path superimposed on a slower scanning movement. The present invention comprises those cases where the transducers for detecting cracks and magnetically disturbing material are placed on or in the same scanning arrangement, which has several advantages. In this way, crack detectors can be blocked to an optimum extent, i.e. to a sufficient extent and for an adequate period of time, since the information about the presence of magnetic material is both up-to-date and exact.

Figure 4:
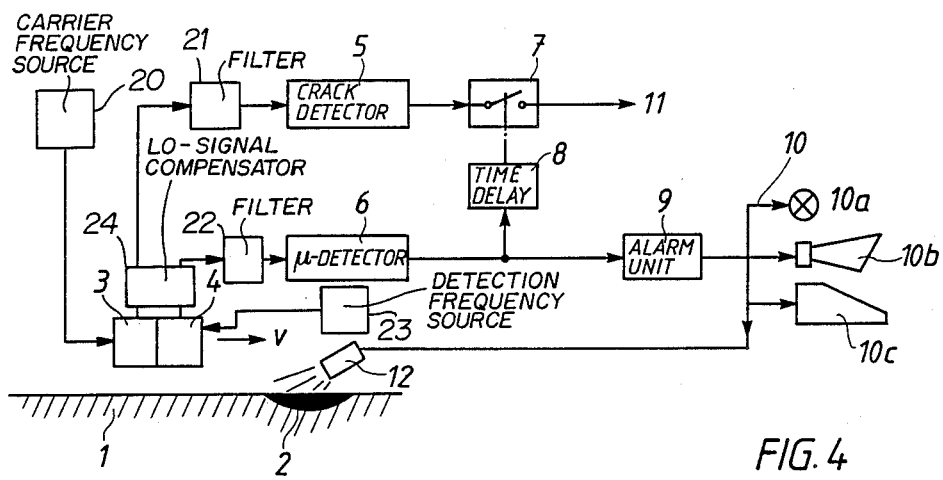
Figure 5:
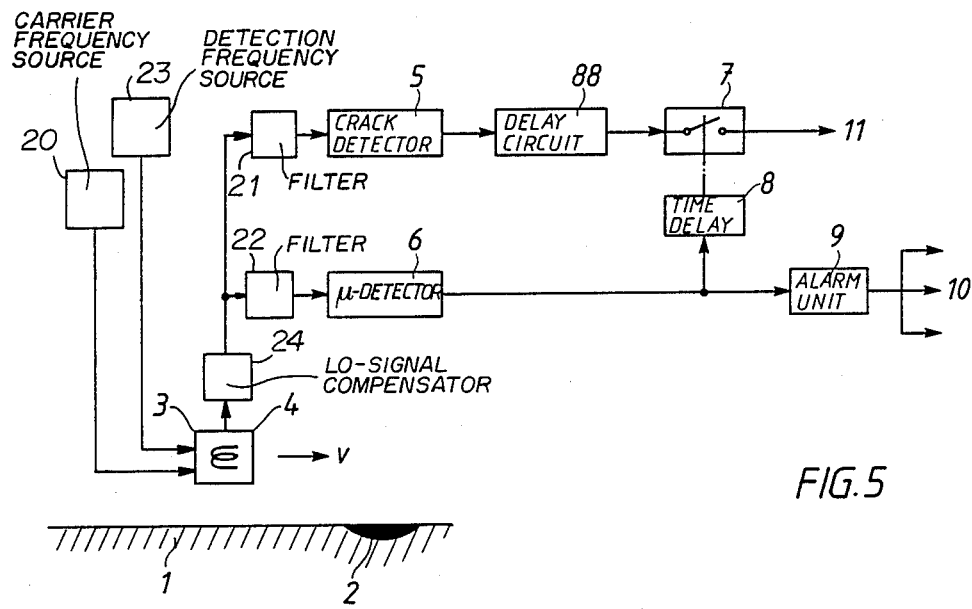

To illustrate how the crack detector and the magnetic detector or $\mu$-detector can cooperate, two largely equivalent block diagrams are shown in FIGS. 4 and 5. Let it be assumed that the test object 1 contains a magnetic oxide scale flake 2. The transducers 3 and 4, which in FIG. 5 consist of a common surface transducer coil, move over the surface of the test object 1. The transducers, which move at the velocity v m/s, consist of one crack transducer 3 and one transducer 4 for $\mu$-detection. The transducers are connected to LO-signal compensator 24 which compensates for and suppresses the presence of a LO vector. The LO-signal compensator 24 can suppress the LO vector by one of several methods: (1) detecting and identifying the vectors largely perpendicular to the LO-direction or FV-direction as $\mu$-vectors; (2) filtering the signals from the transducers 3 and 4 to separate out the frequency component characteristic of the LO-signal; (3) introducing at least one LO-signal or its component originating from a different carrier frequency to balance away the LO-vector or its component; (4) a combination of the three prior methods.

The outputs of LO-signal compensator 24 corresponding to the signals from transducers 3 and 4 are respectively connected to filters 21 and 22 which are turned to the signal frequency contents of the fault vector FV and the $\mu$-vector, respectively. Filters 21 and 22 are, respectively, connected to a crack detector 5 of eddy current type, as disclosed in U.S. Pat. No. 4,646,013 for example, and to a $\mu$-detector 6 of eddy current type for detecting the presence of magnetic material. In accordance with U.S. Pat. No. 4,646,013 transducer 3 is fed with carrier frequencies $\omega_H$ and $\omega_L$ by carrier frequency source 20. For magnetic detection, transducer 4 is fed by detection frequency source 23. In FIG. 5, the common surface transducer coil is fed by carrier frequency source 20 for crack detection and detection frequency source 23 for magnetic detection. The crack detector 5 is connected to a blocking circuit 7, from which crack signals can be obtained at an output 11. In FIG. 5 the crack signal also passes through a delay circuit 88. The output signal from the $\mu$-detector 6 controls the blocking circuit 7 via a time delay unit 8, which may, for example, extend the control signal from the $\mu$-detector 6 so as to obtain an optimum blocking. Different types of alarm signals 10 are given via an alarm unit 9, those shown in FIG. 4 being a light signal device 10a, a sound signal device 10b and a print out device 10c. A particularly good arrangement is to locate the $\mu$-transducer 4 immediately in front of the crack transducer 3 since in this way the crack detector 5 is blocked just before the crack transducer 3 reaches the disturbing region 2. The same end is achieved if, as shown in FIG. 5, the crack signal is delayed in the delay circuit 88, which may consist of an analog shift register or the like. This delay makes it possible for a false crack signal, which has arisen as a result of the flake 2 of magnetic material, to be blocked in a reliable manner by the signal from the $\mu$-detector 6. Because of the delay in the circuit 88 the signal from the $\mu$-detector 6 should be extended by the time delay unit 8, for example by a period somewhat longer than the delay time set by the delay circuit 88.

The invention is also characterized in that alarm signals 10, about the presence of magnetic material, can be used to activate and/or control, for example, a separate device for the removal and/or elimination of the magnetic material and/or a suppression of its effects on, for example, the detection of cracks.

The invention thus embraces the use of a further device 12, for example controlled via an alarm signal 10, for eliminating completely or partially the magnetic properties of oxide scales and the like on, for example, hot test objects, by heating the oxide scales to a temperature corresponding to at least the Curie temperature of the oxide material, which renders the oxide scale largely non-magnetic. This heating can, for example, be achieved by heating up the oxide scales (e.g. using at least one gas burner or gas flame). Another way is to raise the temperature of the oxide scales by means of an inductive heating device. The heating device may advantageously be mounted on the scanning equipment adjacent to the transducer of the measuring and/or control device. Such heating can be initiated, for example, when the $\mu$-detector 4 indicates that the oxide scales are magnetic or are tending to become magnetic. In this way, the heating can take place selectively in places where magnetic oxide scales and the like have become established. By locating the transducers for crack detection and $\mu$-detection and the heating device on the same movable support connected to, for example, a billet strand, for example on a cross travel car, a financially attractive overall solution is obtained.

In summary, the invention comprises providing, for example, a conventional eddy-current based crack-detecting equipment, which is adapted to scan preferably non-magnetic test objects, with a device which detects—for example, advantageously via eddy current technique —the presence of disturbing magnetic material, for example relatively cold magnetic oxide scales, in and/or on the test object in order thus to monitor, for example, that disturbances (i.e. so-called "false" cracks) originating from the presence of magnetic material, are not confused with read cracks and similar harmful surface defects.

In order to avoid too large a proportion of the sensed surface becoming insensitive for crack detection because of excessive magnetic disturbances, the device can be provided with means (for example a heating device) to eliminate the magnetic properties of, for example, oxide scales.

The arrangement described can be varied in many ways within the scope and spirit of the following claims.

What is claimed is:

1. A device for non-destructive detection of harmful faults in a non-magnetic test object and for the detection and suppression of the influence of disturbing magnetic areas comprising at least one fault signal transducer associated with at least one fault sensor adapted to move relative to the test object, at least one magnetic signal transducer associated with at least one detector associated with the fault sensor for detecting the presence of any disturbing magnetic areas, and at least one blocking means for suppressing signals originating from the fault sensor wherein:

the magnetic detector controls the blocking means such that, upon detection of a magnetic area, the blocking means causes the signals from the fault sensor originating from the detection of a magnetic area to be blocked and to not be interpreted as signals originating from a fault.

2. A device according to claim 1, in which information about the presence of magnetic material is used for activating means to effect removal of the influence of the magnetic material.

3. A device according to claim 2, in which the removal of the influence of the magnetic material is effected by one of brushing, air blasting and heating.

4. A device according to claim 1, in which an alarm is provided which is actuated upon detection of a magnetic area on the test object.

5. A device according to claim 1, in which a signal representing the presence of magnetic material is used for suppressing the signal detected by the fault sensor due to the said presence so that a false crack signal is not indicated by the presence of the magnetic material.

6. A device, according to claim 1, in which the fault sensor and magnetic detector both use eddy current techniques.

7. A device, according to claim 6, in which the magnetic properties of any disturbing magnetic area are measured as a function of at least one of the electric impedance and the impedance variation of the fault sensor.

8. A device, according to claim 1, in which the fault signal transducer and magnetic signal transducer create, respectively, at least one fault vector representing the signal outputted by the fault signal transducer that a fault is detected and at least one $\mu$-vector representing the signal outputted by the magnetic signal transducer that a magnetic area is detected.

9. A device, according to claim 1, in which the device is fed with more than one carrier frequency, such that on a normalized impedance diagram at least one carrier frequency is so chosen that a $\mu$-vector does not cross the vector envelope or lobe of possible fault vectors.

10. A device, according to claim 9, in which at least one signal originating from the $\mu$-vector can be separated from at least the majority of signals originating from the fault vectors.

11. A device, according to claim 1, in which lift-off dependence is at least reduced via compensation of the fault signal transducer and magnetic signal transducer output signals by a lift-off signal compensator.

12. A device, according to claim 11, in which lift-off compensation is by the detecting and identifying of at least one vector largely perpendicular to the direction of at least one lift-off vector or the direction of at least one fault factor as a $\mu$-vector.

13. A device, according to claim 11, in which lift-off compensation is by filtering out at least one signal from the fault signal transducer and at least one signal from the magnetic signal transducer to separate out the frequency component characteristic of the signal representing the lift-off vector.

14. A device, according to claim 11, in which lift-off compensation is by introducing at least one lift-off vector signal or its component originating from a different carrier frequency to balance away the lift-off vector to be suppressed or its component.

15. A device, according to claim 1, in which a signal from the magnetic signal transducer originating from a $\mu$-vector and a signal from the fault signal transducer originating from a fault vector are filtered in filters tuned to different specific frequencies.

16. A device, according to claim 15, in which the filter for the fault signal transducer is tuned to at least one specific frequency in order to pass at least one specific frequency component of the signal originating from the fault vector.

17. A device, according to claim 15, in which the filter for the magnetic signal transducer is tuned to at least one specific frequency in order to pass at least one specific frequency component of the signal originating from the $\mu$-vector.

18. A device, according to claim 1, in which at least one signal from the -detector originating from the detection of a magnetic area and representing a detected $\mu$-vector is used for automatically blocking the fault detector.

19. A device, according to claim 1, in which at least one fault vector and at least one $\mu$-vector are adapted to be separated from the other on the basis of a comparison of signals originating from at least two detectors of signal vectors.

20. A device, according to claim 19, in which the signal vector detectors are substantially similarly constructed but differently adjusted.

21. A device, according to claim 19, in which only two signals, a high frequency and a low frequency, are used per signal vector detector.

22. A device, according to claim 19, in which at least two similar input signals are used in at least two signal vector detectors.

23. A device, according to claim 19, in which at least one signal outputted from a signal vector detector is signal processed so that disturbing irregularities can be suppressed.

24. A device, according to claim 19, in which the signal vector detectors are of eddy current type.

25. A device, according to claim 23, in which the suppression of disturbing irregularities is done by the blocking of a signal outputted by a first signal vector detector by the signal processing of a signal outputted by a second signal vector detector.

* * * * *